United States Patent [19]
Williams

[11] 3,985,508
[45] Oct. 12, 1976

[54] AUTOMATED CHEMICAL ANALYZER

[76] Inventor: Melvin Williams, 840 Elmwood, Evanston, Ill. 60202

[22] Filed: Oct. 28, 1975

[21] Appl. No.: 626,053

[52] U.S. Cl. .............................. 23/253 R; 23/259
[51] Int. Cl.² ......................................... G01N 31/00
[58] Field of Search ......................... 23/253 R, 259

[56] References Cited
UNITED STATES PATENTS

| 3,193,358 | 7/1965 | Baruch | 23/253 R |
|---|---|---|---|
| 3,533,744 | 10/1970 | Unger | 23/253 R X |
| 3,544,272 | 12/1970 | Vails | 23/253 R |
| 3,615,239 | 10/1971 | Jones et al. | 23/253 R X |
| 3,728,079 | 4/1973 | Moran | 23/253 R |
| 3,756,783 | 9/1973 | Williams | 23/253 R |
| 3,799,744 | 3/1974 | Jones | 23/253 R |
| 3,802,782 | 4/1974 | Natelson | 23/253 R X |
| 3,883,305 | 5/1975 | Hoskins et al. | 23/253 R |
| 3,917,455 | 11/1975 | Bak et al. | 23/253 R |

Primary Examiner—Robert M. Reese
Attorney, Agent, or Firm—Merriam, Marshall, Shapiro & Klose

[57] ABSTRACT

Apparatus for automatically performing multiple chemical analyses of a plurality of liquid specimens. The apparatus comprises apparatus for loading a plurality of test samples from each specimen into a row of reaction vessels. As the reaction vessels are transported to a determinating apparatus, other apparatus adds reagents to preselected ones of the reaction vessels a predetermined time before the reaction vessels reach the determinating apparatus. In particular, each of the several sample containers initially containing the specimens is transported in a track or the like in parallel with the one of the several rows of reaction vessels containing the test samples from the specimen toward the determinating apparatus. Microswitches engage each of the sample containers along the way, enabling the reagent adding apparatus to add selected reagents to the parallel row of reaction vessels. The reacted test samples are automatically analyzed by the determinating apparatus and the results output on a paper tape or the like. In addition, apparatus is provided for automatically removing the sample containers from the track after the determinations have been completed and depositing the containers in predetermined sequential order in a tray.

22 Claims, 15 Drawing Figures

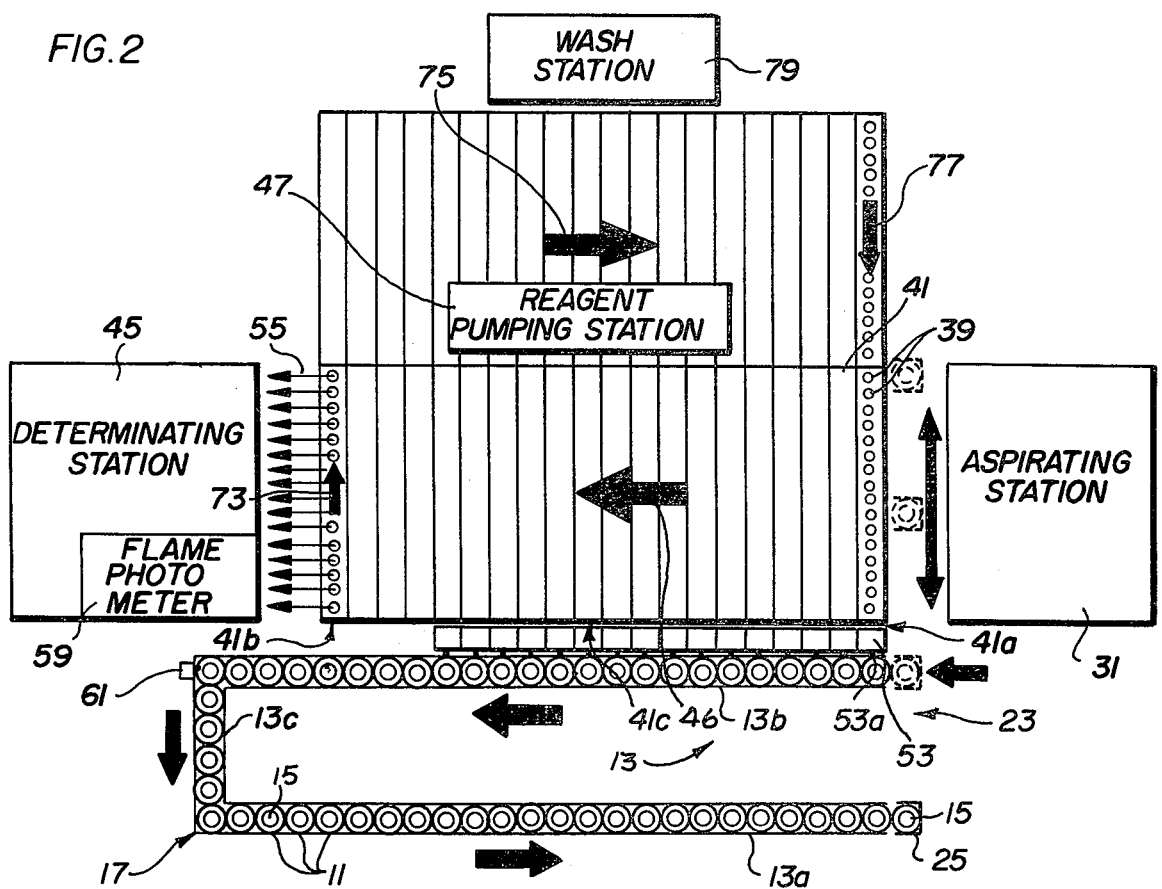
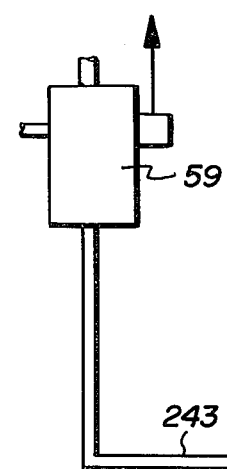
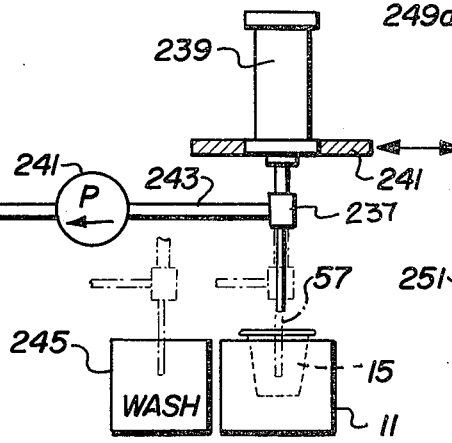
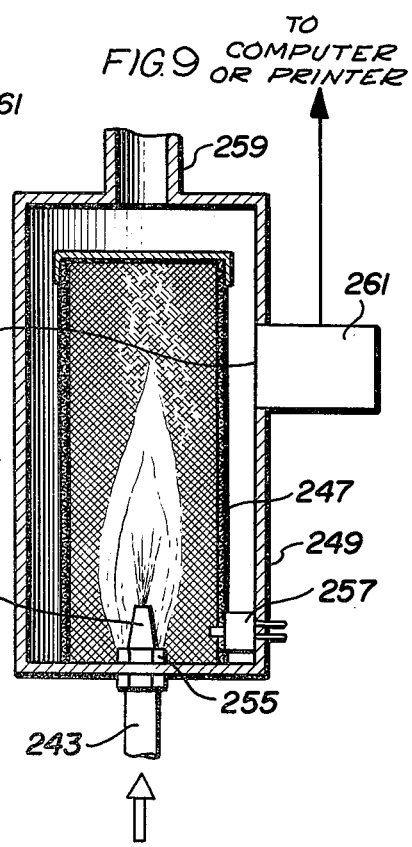

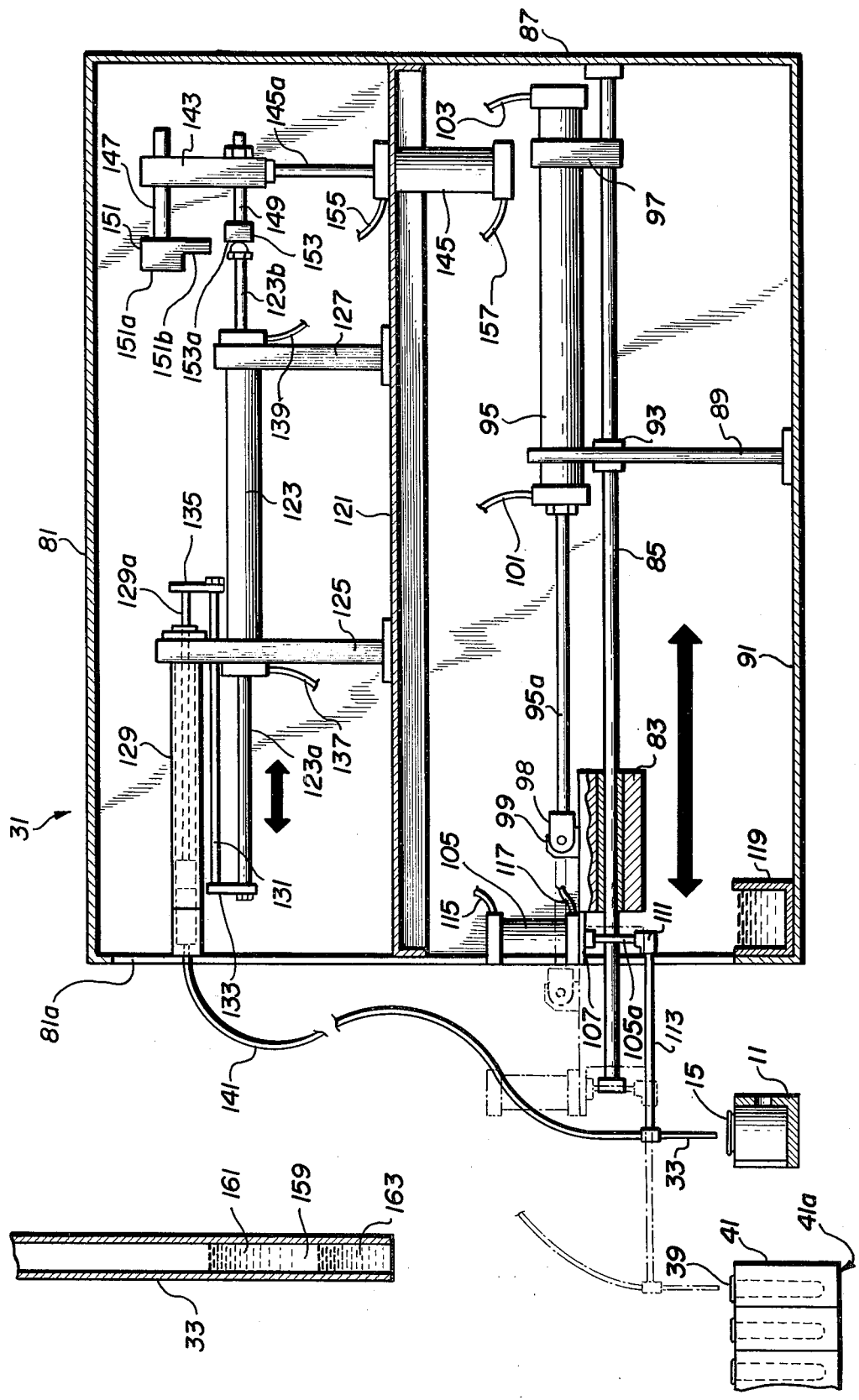
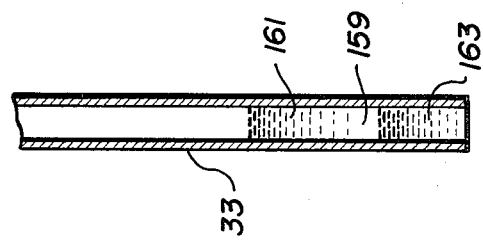

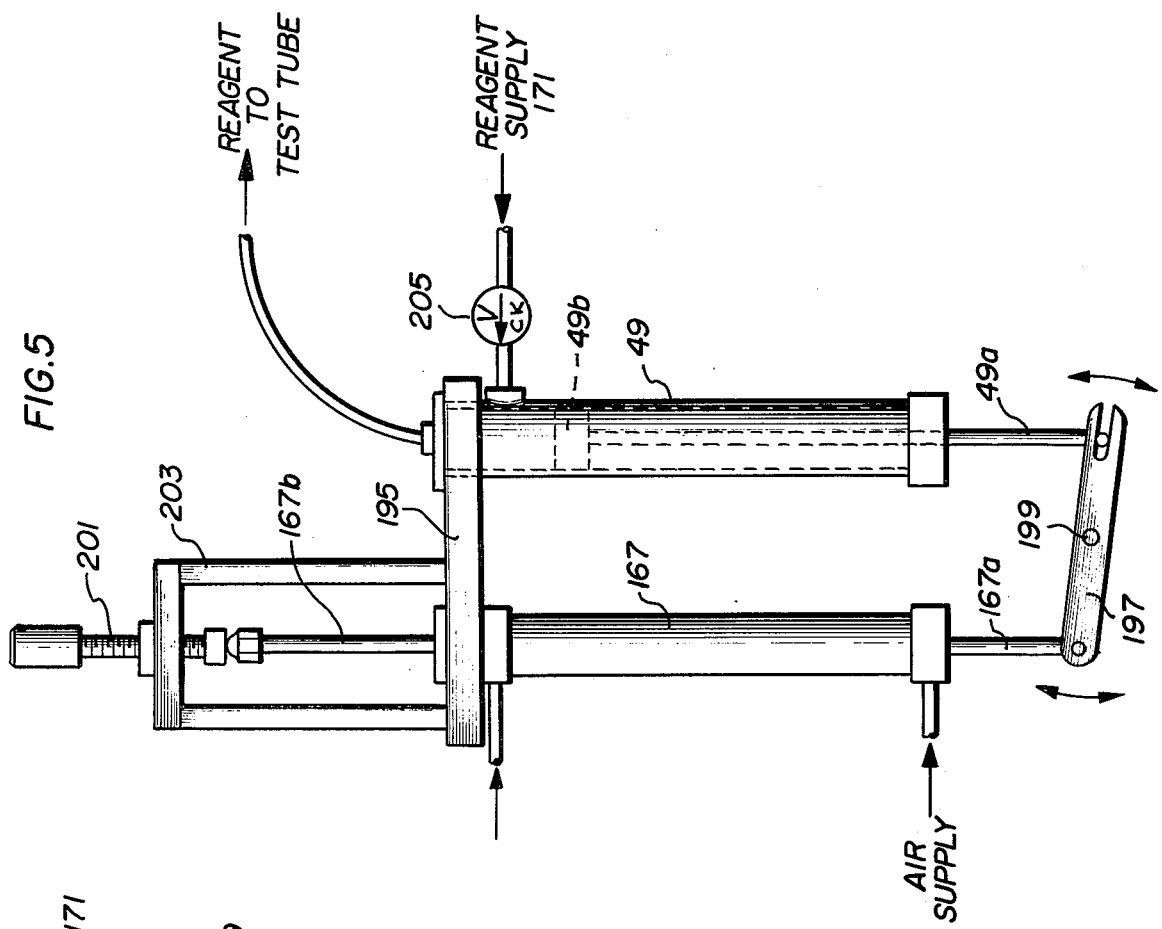
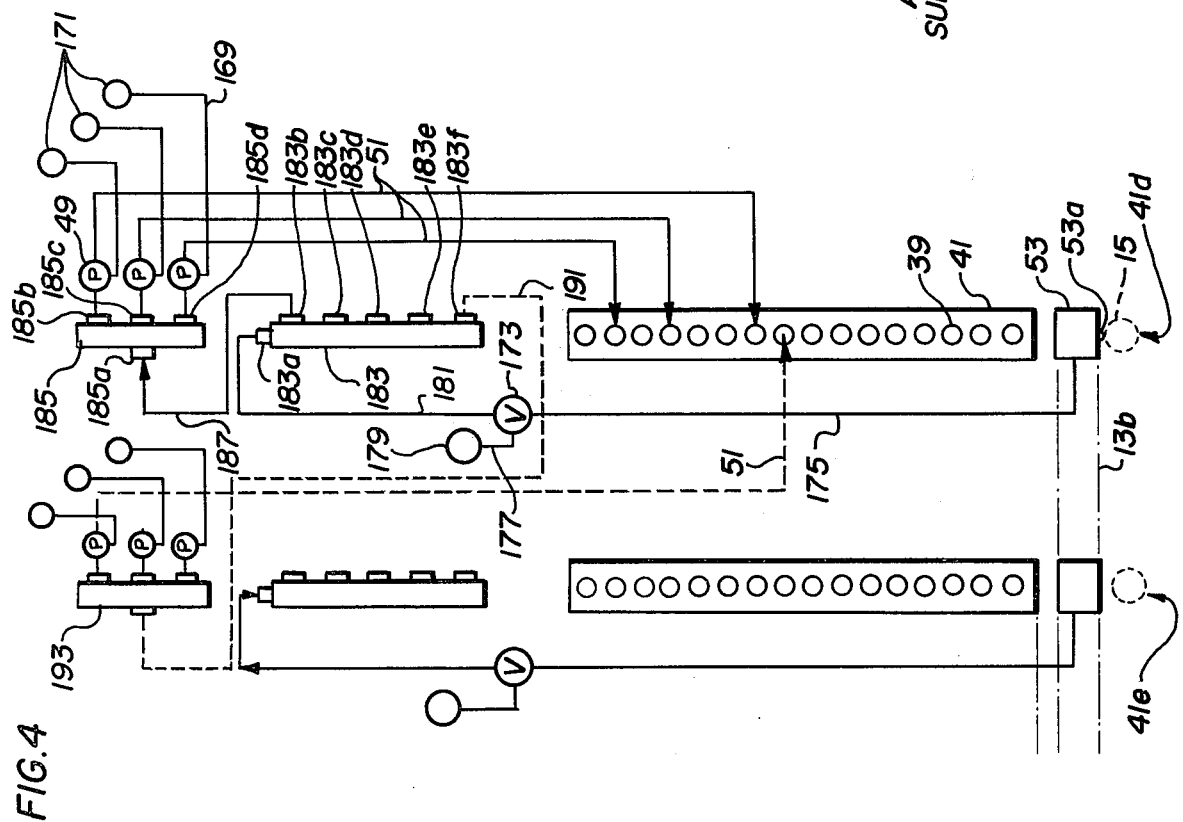

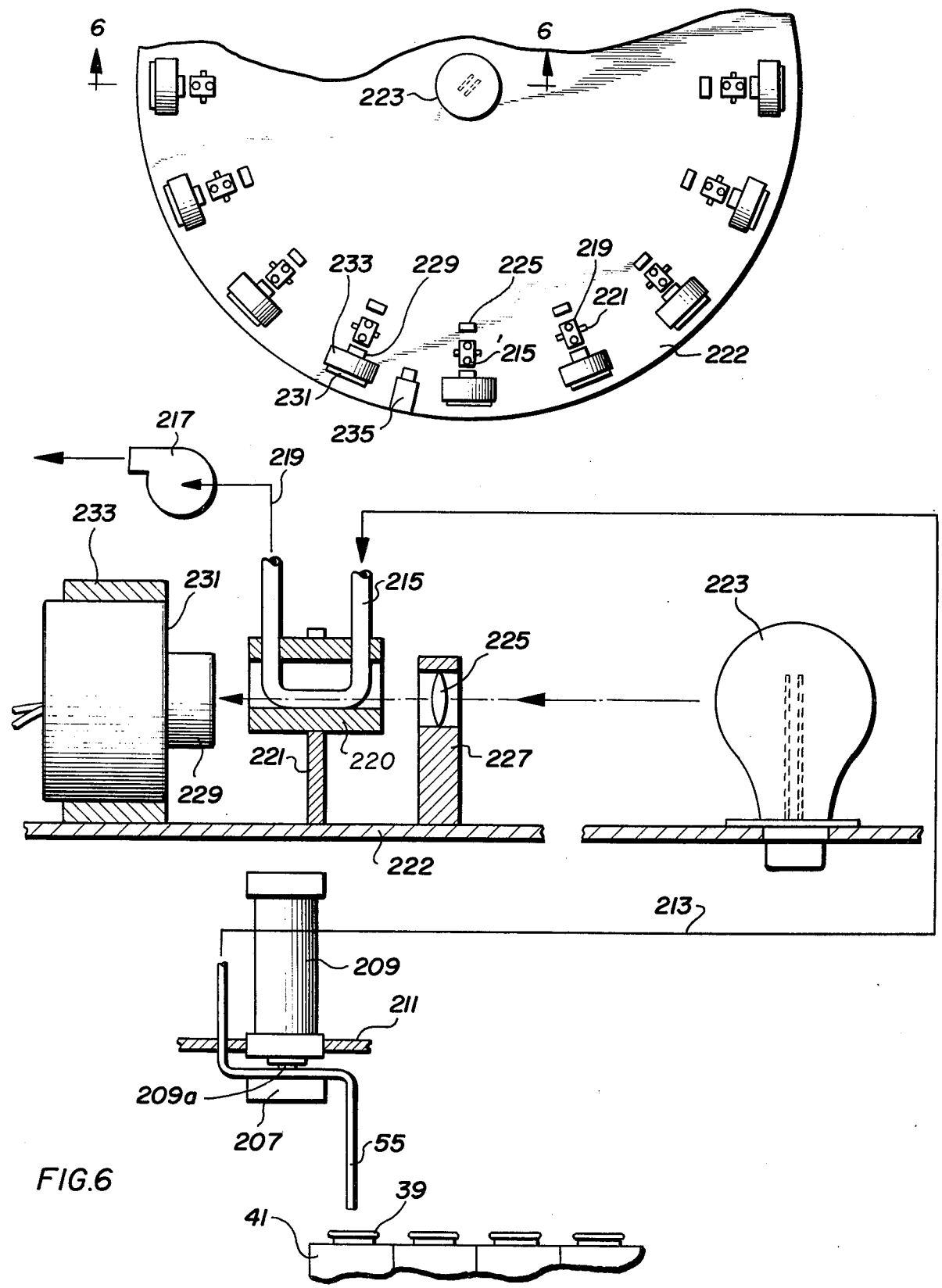

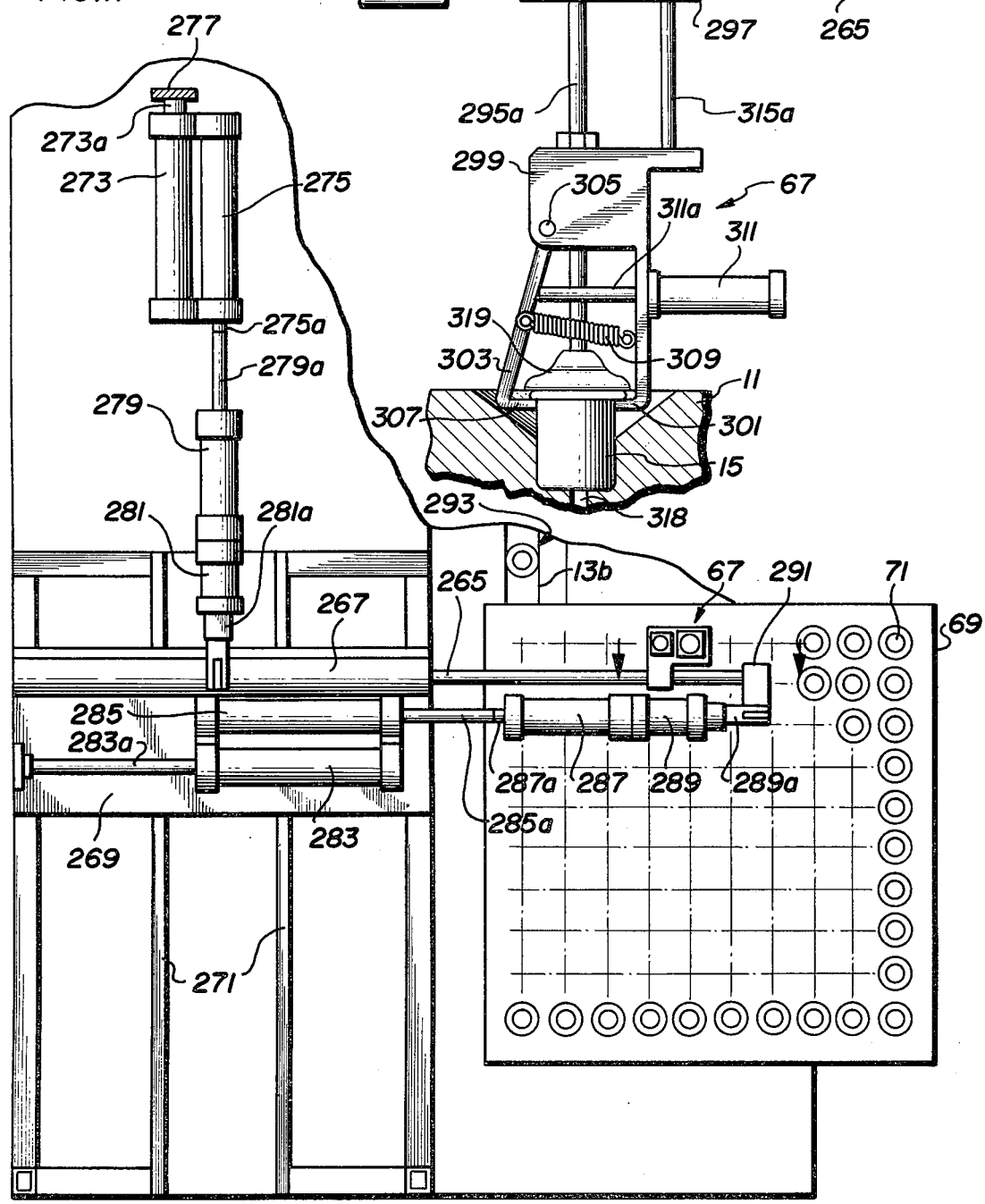

AUTOMATED CHEMICAL ANALYZER

This invention relates generally to automated chemical analyzers and more particularly to apparatus for automatically performing multiple chemical analyses of liquid specimens.

Various automated mechanical apparatus have heretofore been suggested for conducting chemical analyses of liquid specimens. One example of an automated chemical analyzer may be found in my U.S. Pat. No. 3,756,783, issued Sept. 4, 1973. Reference should also be made to the following relevant United States Patents wherein other automated analytical apparatus are described in detail: 3,728,079; 3,799,744; 3,883,305; 3,615,239; and 3,193,358.

Although the automated chemical analyzer of the present invention as hereinafter described may find many applications in the laboratory and in industry, it is especially well suited for clinical use in the medical field where analyses of liquid specimens such as blood, urine, and the like must be performed in great numbers, but with accuracy and precision in accordance with standard analytical procedures.

For example, in a large metropolitan hospital, literally thousands of specimans must be analyzed each day with each specimen undergoing anywhere from one test to a complete battery of tests. Due to the large number of tests which must be performed as well as circumstances where the condition of the patient requires, speed is also of utmost importance. The demands for time and manpower to perform the analyses may become overwhelming, resulting occasionally in erroneous determinations due to human error related to haste, fatigue, and other such factors. Such errors include but are not limited to failure to run the test properly or erroneously attributing the test results to the wrong patient when recording the results. It goes without saying that such errors may result in diagnostic errors in crucial life and death situations.

As a result, automated chemical anaylzers have been developed to, inter alia, alleviate the problems just described. However, these apparatus have generally been complex, specialized machines limited in the number and range of analytical tests they are capable of performing while also being rather costly. Although they may find acceptance in larger facilities, their complexity and resultant higher cost may be a prohibitive factor where smaller hospitals and medical facilities are concerned.

Accordingly, to enjoy a wide degree of commercial acceptance among all sizes and types of medical facilities having use for an automated chemical analyzer, such an analyzer should provide the same or greater testing capability but in a simpler machine and at lower cost than the complex machines heretofore developed. The automated chemical analyzer should be simpler to operate and flexible so that the program of chemical analyses being run can be changed quickly and without difficulty. The apparatus should be accurate and precise. Moreover, means should be provided for positive sample identification so that test results are correctly identified with the patient from whom the sample was obtained.

Therefore, in accordance with the principles of the present invention, there is provided apparatus for automatically performing multiple chemical analyses of a plurality of discrete liquid specimens utilizing any one or more of a number of reagents. The apparatus, being totally automated and including a positive sample identification feature, eliminates specimen mix-up and other errors related to manual or semi-manual testing and is easy to operate, requiring no specialized training.

The apparatus in one of its embodiments is capable of selectively performing from one to eighteen determinations of a single specimen in accordance with an analysis program that can be varied to include any of the classical methodologies used in the clinical laboratory. Accordingly, the apparatus is not locked in to a single method but indeed may be used in a wide range of applications including but not limited to routine lab work, profile analysis and in the STAT lab, emergency lab and pediatric lab. Although other embodiments constructed in accordance with principles of the invention may be capable of performing more or fewer tests on each specimen, the apparatus hereinafter illustrated and described is capable of analyzing up to 120 specimens per hour, performing a maximum of 2160 determinations, with a dwell time to output of twenty-one minutes. The apparatus performs colorimetric endpoint, flame photometric and ultraviolet kinetic analyses of the specimens. Moreover, the apparatus requires only an average of 20 microliters of specimen for each determination with a range of between 5 and 50 microliters, a total volume of less than one milliliter. Accordingly, the consumption of chemical reagents is significantly reduced since the reagents are also added in microliter volumes.

More particularly, the apparatus includes means comprising a delivery track for sequentially conveying specimen-bearing sample containers to a transfer apparatus which steps the sample containers past an aspirating apparatus. A return track conveys the track containers from the transfer apparatus after the aspirating means have automatically aspirated a plurality of test samples from the sample container. The test samples are subsequently released by the aspirating apparatus into corresponding reaction vessels. Means are also provided for transporting the reaction vessels in a closed loop between the aspirating apparatus and a determinating station, all of the reaction vessels containing the test samples aspirated from a particular specimen being transported in rows from the aspirating apparatus to the determinating station in parallel with the sample container from which the test samples were aspirated. Means for selectively adding predetermined amounts of selected reagents are controlled by other means comprising a plurality of switching devices adjacent the return track between the return track and the rows of reaction vessels being transported to the determinating position. In particular, the switching devices are sequentially enabled by the sample cup being returned on the return track in parallel with the corresponding row of reaction vessels containing the test samples aspirated from the sample cup, and responsively, the reagent dispensing means adds one or more reagents to selected reagent vessels in accordance with a pre-selected program. Additional means are included for aspirating the reacted test samples from the reaction vessels at the determinating station and automatically performing multiple chemical analyses of the reacted test samples and outputting the results of the analyses. The test results may be printed out on a paper tape, or alternatively, coupled to a computer for compilation and/or diagnostic evaluation.

Further novel aspects of the present invention include means for automatically removing the sample cups from the return track after the determinations on the corresponding test samples have been completed and depositing the cup in a predetermined, identifiable, sequential order in a tray. Also included are means for washing and drying the reaction vessels after each determination has been completed. Other aspects of the conveyor means, the transfer means, the reagent dispensing means, including the switching means, the determinating means and the washing means are also considered to be novel and are hereinafter more fully described.

FIG. 2 is a schematic plan view of apparatus of FIG. 1;

FIG. 3 is an elevational view, partly in section, illustrating a pickup probe and related probe positioning and other apparatus comprising transfer means, for aspirating a test sample from the specimen in a sample cup and discharging the sample into a reaction vessel;

FIG. 3A is a sectional, elevational view of the pickup probe in FIG. 3;

FIG. 4 is a schematic plan view illustrating the reagent dispensing apparatus and the switching means controlling the dispensing of reagents to the reaction vessels in a manner establishing a program determining the particular analyses being performed and further illustrating how the program is selectively changed to perform other desired analyses;

FIG. 5 is an elevational view illustrating a single pumping apparatus in the reagent dispensing apparatus shown in FIG. 4;

FIG. 6 is an elevational view, partly in section and partly in schematic, illustrating a single pickup probe and determinating apparatus for aspirating reacted test samples from the reaction vessels and automatically performing the determinations;

FIG. 7 is a partial top plan view illustrating the arrangement of a plurality of the determinating apparatus shown in FIG. 6;

FIG. 8 is an elevational view illustrating sample pickup apparatus for supplying unreacted specimen sample to a flame photometer apparatus;

FIG. 9 is a sectional, elevational view illustrating the flame photometer apparatus;

FIG. 10 is a top plan view in section of the flame photometer apparatus in FIG. 9;

FIG. 11 is a top plan view illustrating an apparatus for automatically removing the sample cups from the return track and depositing the cups in a tray in sequential order to maintain a correlation between the particular specimen tested and the test results;

FIG. 12 is an elevational view, partly in section, illustrating a pickup mechanism included in the apparatus shown in FIG. 11;

Figure 1:
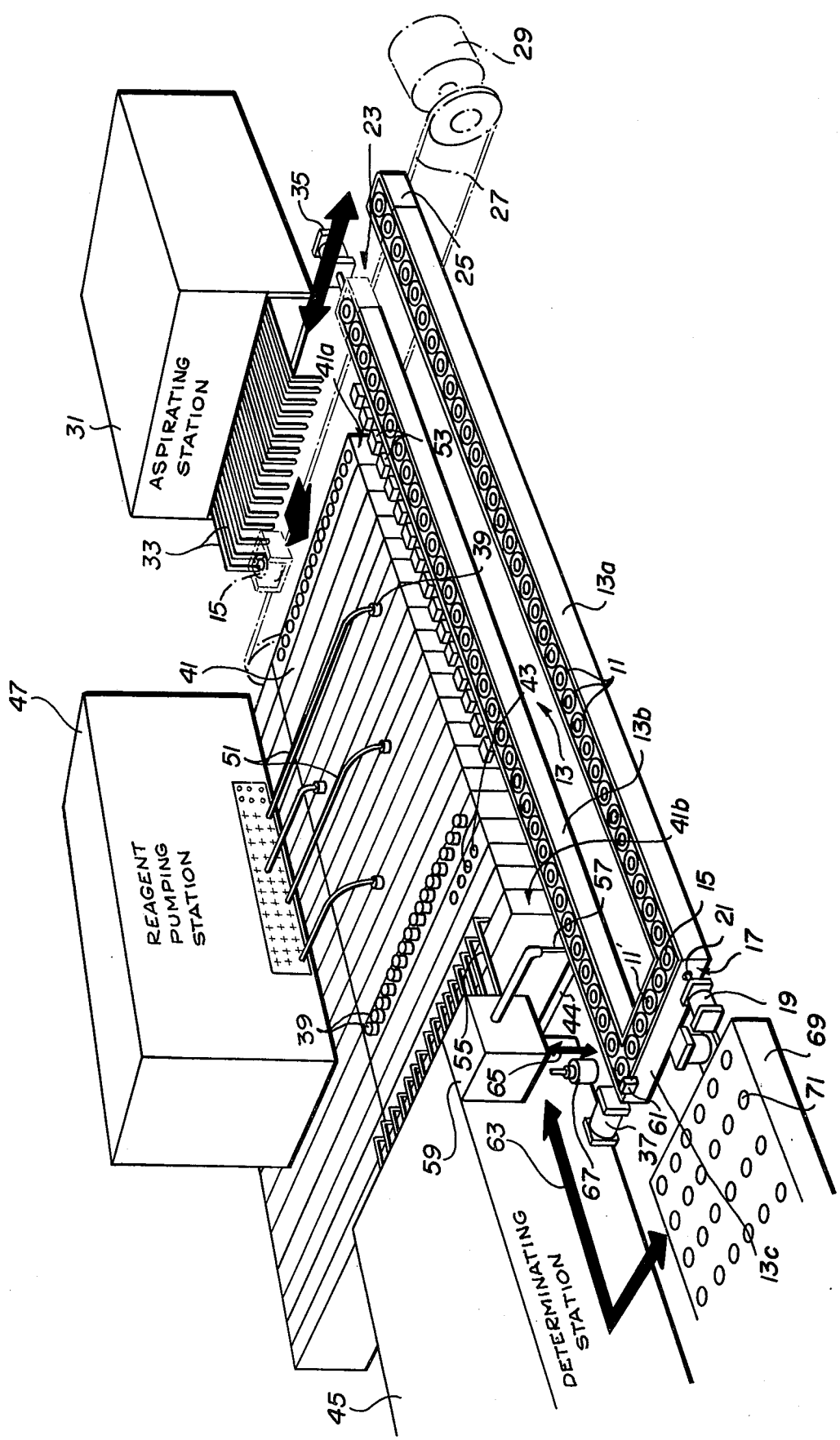
FIG. 1 is a perspective view of the apparatus for automatically performing chemical analyses in accordance with the present invention.

Referring now to FIGS. 1 and 2, there is shown as hereinafter described an automated chemical analyzer for automatically performing multiple chemical analyses of liquid specimens such as blood, urine or the like in accordance with the present invention. The analyzer apparatus generally comprises apparatus for conveying the specimen to be analyzed to aspiration apparatus where one or more aliquot test sample portions of the specimen are selectively transferred into reaction vessels which, in turn, transport the test samples to a determinating station while reagents are selectively added to the samples at predetermined points along the way. At the determinating station, various determinations of the reacted test samples are performed to provide a comprehensive profile analysis of the specimen under test. The test results are then printed out on a paper tape, or alternatively, coupled to a computer for compilation and/or diagnostic evaluation before being outputed.

In particular, the apparatus includes a plurality of cylindrical receptacles 11 which are transported along a U-shaped conveyor track 13 comprising an outer delivery track portion 13a, an inner return track portion 13b, and an end track portion 13c interconnecting the delivery and return tracks. Each receptacle 11 has a cavity 11' therein suitable for receiving and holding a sample cup or container 15 initially containing a corresponding liquid specimen that is to be analyzed. In the present embodiment, the specimen-containing sample cups 15 are manually placed in the receptacles 11 at an initial loading position, identified generally at 17, along the conveyor track 13. Although in the present embodiment the loading position is shown at the left end of the delivery track 13a, it will be understood in view of the following description that the initial loading position can be at any point or points along the delivery track 13a or the end track 13c. Once in the receptacles 11, the sample cups 15 are automatically transported along the U-shaped conveyor track 13.

When the analyzer apparatus is operational, the receptacles 11 in the delivery track 13a are pushed from left to right, as indicated in FIG. 2, at periodic intervals, by a pneumatic cylinder 19 located adjacent the left end of the delivery track 13a. The piston rod of the pneumatic cylinder 19 extends through an aperture 21 in the side wall of the end track 13c and is operable to move in a reciprocal manner to push the immediately adjacent receptacle, and hence the other receptacles 11, in the delivery track 13a toward a sample transfer apparatus, identified generally at 23, at the right end of the delivery track 13a. Upon reaching the transfer apparatus 23 in the normal sequence of operation, the specimen-bearing receptacle 11 is pushed into a trolley 25 which is initially aligned with the open end of the delivery track 13a. The trolley 25 is mounted on a chain conveyor belt 27 driven by a reversible stepping motor 29, and after the receptacle 11 is positioned in the trolley 25, the stepping motor 29 is enabled to transport the receptacle 11 and the sample cup 15 contained therein laterally to an aspirating station or apparatus 31.

The aspirating station 31 comprises a plurality of selectively actuable test sample pickup probes 33 which aspirate aliquot portions of the liquid specimen, e.g., 5–50 μl, from the sample cup 15. As the trolley 25 is stepped past the probes 33 by the stepping motor drive apparatus, the sample cup 15 pauses immediately adjacent each pickup probe 33 for a predetermined period of time, e.g., one second, while the aliquot test sample portion is aspirated before the sample cup 15 is repositioned adjacent the next probe 33.

After the sample cup 15 has been transported to the last pickup probe 33 and the test samples aspirated, the stepping motor 29 is reversed to return the trolley 25 to a point where it is aligned with the open end of the return track 13b. The receptacle 11, together with the sample cup 15 therein containing the left-over specimen, is then pushed from the trolley 25 into the open end of the return track 13b by a pneumatic cylinder 35. That is, the periodic reciprocal motion of the piston rod of the cylinder 35 extending through an aperture in the back wall of the trolley 25 pushes the receptacles 11 along the return track 13b as the trolley 25 delivers subsequent receptacles 11 to the end of the return track 13b. After the receptacle 11 carrying the sampled specimen is removed, the trolley 25 is repositioned immediately adjacent the open end of the delivery track 13a to receive the next specimen-bearing receptacle 11 in the operational sequence.

At the left end of the return track 13b, the receptacle 11 advanced to the end of the return track 13b by the pneumatic cylinder 35 is pushed from the return track 13b into the end track 13c, by a pneumatic cylinder 37 aligned with the end track 13c, moving another receptacle 11 preceding it into the previously vacated initial loading position 17. There, a new specimen-bearing sample cup 15 is loaded into the receptacle 11a. When pneumatic cylinder 19 is next actuated, the next receptacle 11 in the sequence at the transfer apparatus 23 is loaded into the trolley 25. Thus, the pneumatic cylinders 19, 35 and 37 cooperate to push the receptacles along the U-shaped track 13, each receptacle 11 being moved into the position vacated by the receptacle 11 immediately preceding it in the track. Accordingly, in the present embodiment, the receptacles 11, and hence the sample cups 15, are circulated in a counterclockwise direction along the U-shaped track 13.

After the aliquot test samples have been aspirated from the sample cups 15 by the sample pickup probes 33, the probes 33 are moved forward simultaneously to release the test samples and a diluent such as water into a corresponding plurality of reaction vessels 39, e.g., test tubes, arranged in a parallel row in cavities 43 along the length of a block 41. In the present embodiment, for example, the aspirating station 31 comprises sixteen pickup probes 33, and accordingly, each block 41 carries sixteen reaction vessels 39 to receive the aspirated test samples. A plurality of the rectangular blocks 41 are used to transport the test samples corresponding to a plurality of specimens on a controlled temperature bed 44 to a determinating station 45. The bed 44 comprises a thermo-heating block controlled at ±0.05°C. having selectively variable heating zones for heating the test samples to required temperatures at various points along the way as required by the particular tests being performed.

As may be seen most clearly in FIG. 2, the blocks 41 are moved in a clockwise direction in a closed loop from the aspirating station 31 to the determinating station 45 and back to the aspirating station 31. In the particular embodiment illustrated in FIGS. 1 and 2, pneumatic means shown schematically by block arrow 46 are provided to move each block 41 through twenty positions including the positions 41a and 41b immediately adjacent the aspirating and determinating stations 31 and 45, respectively, between the aspirating station 31 and the determinating station 45. As the reaction vessels 39 are transported to the determinating station 45, each block 41 pauses for a predetermined period of time, e.g., thirty seconds in the present embodiment, at each of the several intermediate positions before advancing to the next adjacent position.

At each position, reagents may be selectively introduced into the reaction vessels 39 by a programmable reagent pumping station 47 to react with the test samples according to a predetermined operating program. In particular, the reagent pumping station 47 includes a plurality of pneumatically actuated pumps for pumping selected reagents into the reaction vessels 39 at predetermined times, i.e., positions, via reagent lines 51 disposed in preselected positions over the blocks 41 as the reaction vessels 39 are transported to the determinating station 45.

Control of the reagent pumping station 47 is effected by a plurality of microswitches 53 located immediately adjacent and between the return track 13b and the reaction vessel blocks 41. It will be more clearly understood by reference to FIG. 2 that the block 41 containing the aliquot test sample portions of a particular specimen will be transported from right to left in synchronism with and immediately adjacent the receptacle 11 in the return track 13b bearing the sample cup 15 containing the remaining specimen from which the aliquot portions were taken. That is, the block 41 containing the test samples and the sample cup 15 containing the remaining specimen travel in parallel. The switch actuating elements 53a of the microswitches 53 located between the blocks 41 and the return track 13b are positioned to contact the sample cup 15, if one is present, in the receptacle 11 adjacent the microswitch 53 in the return track 13b. Thus, as a particular sample cup 15 is transported along the return track 13b, the microswitches 53 will be sequentially activated on a time basis. The microswitches 53, in turn, control the pumps comprising the reagent pumping station 47. For example, if in performing a particular test a reagent is to be added to one of the reaction vessels 39 five minutes before it reaches the determinating station 45, the pumping station 47 is programmed to introduce the appropriate reagent into the particular vessel 39 when the corresponding sample cup 15, and hence the block 41 with the reaction vessel 39 containing the test sample, reaches the appropriate intermediate position 41c which is five minutes' travel time from the determinating station 45 where the sample cup 15 actuates the corresponding microswitch 53. By the time the block 41 reaches the determinating station 45, all of the chemical reactions are completed.

At the determinating station 45 each one of a plurality of sample probes 55 removes a portion of the reacted test sample from a corresponding one of vessels 39 for testing purposes. In operation, the probes 55 are lowered into the vessels 39 and aspirate a portion of the test samples therefrom for delivery to additional apparatus in the determinating station 45 which performs the various analytical determinations. For example, the determinations may include colorimetric analysis and 3-point ultraviolet kinetic analysis of the glucose, total protein, and albumin contents as well as many other components.

Simultaneously, tests are performed on the portion of the pure specimen remaining in the sample cup 15 at a position on the return track 13b parallel to or after the determinating position 41b. Apparatus including a sample probe 57 located adjacent this cup position aspirates a portion of the unreacted specimen from the sample cup 15 and directs it to a flame photometer 59 where the sample is burned to determine its sodium and potassium component contents. The test data from the determinating station 45 and the flame photometer 59 is then fed into a computer for further analysis and display or, alternatively, the test results may be simultaneously printed out on a paper tape or the like.

Subsequently, the receptacle 11 is pushed to the end of the return track 13b where the sample cup 15 activates a microswitch 61 which, in turn, enables an X-Y pickup apparatus, illustrated schematically by block arrows 63 and 65 in FIG. 1, to remove the sample cup 15 from the receptacle 11 and place it in a sample tray 69. More particularly, the pickup apparatus includes an X-Y positioning means 63 for positioning a pickup mechanism 67 over the return track 13b and vertical positioning means 65 for lowering the pickup mechanism 67 to lift the sample cup 15 from the receptacle 11. The X-Y positioning means 63 then transports the sample cup 15 to the sample tray 69 where the cup is deposited in one of a plurality of cavities 71 in the tray. In accordance with one aspect of the present invention, the sample cups 15 are removed from the receptacles 11 in sequence and stored in consecutive order in the tray 69 so that a correlation is preserved between the particular specimen tested and the test results printed out. More particularly, the first sample cup 15 is picked up by the apparatus 63 from the return track 13b after testing is completed and transported to the hole 71 in the first row and the first column of the tray 69. Subsequently, the next cup 15 is removed from the track 13b and delivered to the next hole in the first row. This procedure continues with the rows being filled sequentially so that a correlation between the sample cups 15 (and hence the patient) and the printed test results read-out can be maintained. Accordingly, if an abnormal or unexpected result is obtained, the corresponding sample cup 15 can be retrieved and additional tests performed, either by the analyzer apparatus or manually, to confirm or disprove the original results.

After the test samples have been removed from the reaction vessel 39, pneumatic means, represented schematically herein by block arrow 73, transport the block 41 laterally from the determinating position 41b to a position immediately adjacent thereto. Other pneumatic means (block arrow 75) are provided for then transporting, i.e., pushing, the block 41 toward the aspirating station 31, also pushing the other blocks 41 preceding it toward the aspirating station 31. When the block 41 reaches the position adjacent the aspirating position 41a, additional pneumatic means (block arrow 77) push the block 41 laterally into the aspirating position 41a vacated by the block 41 immediately preceding it.

During the time the blocks 41 are being transported from the determinating station 45 back to the aspirating station 31, the reaction vessels 39 carried therein are automatically washed at a washing station 79 which alternately flushes the vessels 39 with water and then aspirates the water therefrom to clean the vessels 39 in preparation for receiving the next specimen for testing.

With reference now to FIG. 3, the sample aspirating station 31 is shown and described in greater detail. In particular, the cross-sectional view of aspirating station apparatus shown in FIG. 3 illustrates a single one of the several sample pickup probes 33 and its associated apparatus.

The aspiration apparatus comprises a housing, identified generally at 81, containing the sample pickup probes 33 and associated apparatus used in removing an aliquot test sample portion of the specimen from the sample cup 15 as the cup pauses at the aspirating position 41a immediately adjacent one of the sample pickup probes 33.

The pickup probe 33 is supported by a platform 83 slidably mounted on a slide rail 85 extending horizontally from the back wall 87 of the housing out through an opening 81a in the front wall. The rail 85 is attached to the back wall 87, and a support member 89 attached to and extending up from the housing floor 91 supports the slide rail 85 intermediate its two ends in a bushing 93 through which the slide rail 85 extends.

The positioning of the slide platform 83, and hence the probe 33, along the rail 85 in the horizontal direction is controlled by a pneumatic cylinder 95 which is mounted immediately above and in alignment with the slide rail 85 by an extension of the support member 89 and a second support member 97 extending upwardly from the slide rail 85. The piston rod 95a of the pneumatic cylinder 95 extends forward therefrom and has a clevis 98 at its end which attaches to a flange 99 extending from the top surface of the slide platform 83. A pair of hoses 101 and 103 couple compressed air to and from the pneumatic cylinder 95 to control the positioning of the piston in the pneumatic cylinder 95 to permit selective control of the horizontal movement of the slide platform 83 along the slide rail 85.

The vertical positioning of the probe 33, on the other hand, is controlled by a pneumatic cylinder 105 mounted on a flange 107 extending horizontally from the front edge of the slide platform 83. The piston rod 105a of the pneumatic cylinder extends downwardly through an aperture in the flange 107 and is moveable in the vertical direction. An elbow member 111 is attached to the end of the piston rod 105a while a support arm 113 attached to the other end of the elbow member 111 extends outwardly to support the sample probe 33 mounted at the end of the arm 113. The pneumatic cylinder 105 is selectively actuated by pumping compressed air into or releasing air from the cylinder through a pair of air hoses 115 and 117 to effect vertical movement of the piston rod 105a and corresponding movement of the sample probe 33 in the vertical direction.

Accordingly, it will be understood that by selective control of the pneumatic cylinders 95 and 105, respectively, movement of the sample probe 33 in the horizontal and vertical directions can be controlled as desired. Thus, in the present embodiment, the probe 33 is initially positioned to aspirate a predetermined volume of a diluent such as water from a diluent reservoir 119 located adjacent the front wall of the housing 81. The probe 33 is then repositioned over the sample cup 15 to aspirate a predetermined volume of the specimen from the cup, and finally, the probe 33 is extended fully outward from the housing 81 to discharge the diluent and the aliquot test sample portion of the sample into the corresponding reaction vessel 39.

The pumping apparatus comprising the remainder of the aspirating apparatus is supported on a platform 121 immediately above the pickup probe positioning apparatus. More particularly, the pumping apparatus comprises a pneumatic cylinder 123 which is supportably mounted at either end by a pair of support members 125 and 127 extending upwardly from the platform 121 and attached thereto. The support member 125 also extends above the pneumatic cylinder 123 to support a pump 129 in fixed relation therewith above the pneumatic cylinder 123. A first piston rod 123a attached to the pneumatic cylinder piston extends from the left end of the pneumatic cylinder 123 and is coupled to the pump piston rod 129a by a horizontal rod 131 interconnecting vertical tie members 133 and 135 extending from the ends of the pneumatic cylinder and pump piston rods, 123a and 129a, respectively. It will be apparent that any movement of the pneumatic cylinder piston rod 123a results in a corresponding movement of the pump piston rod 129a in the same direction. Thus, control of the pump 129 is effected through control of the pneumatic cylinder 123 by compressed air through hoses 137 and 139. A flexible hose line 141 couples the other end of the pump 129 directly to the sample probe 33.

Mounted adjacent the pneumatic cylinder 123 and aligned with a second piston rod 123b extending from the other end of the cylinder is a calibration apparatus for limiting the movement of the second piston rod 123b to control the amount of specimen and diluent aspirated by the pump 129 and delivered thereby to the reaction vessel 39. In particular, the calibration apparatus comprises a vertical support member 143 mounted on the upwardly extending piston rod 145a of a vertically positioned pneumatic cylinder 145 mounted on the platform 121. The support member 143 has a pair of horizontal rods 147 and 149 extending therefrom toward the second piston rod 123b. A pair of stop members 151 and 153 are located at the end of the rods, 147 and 149, respectively, to contact the end of the second piston rod 123b and limit the travel of the rod. The stop member 151 has a first contact surface 151a for engaging the second piston rod 123b to thereby limit its horizontal travel at a first point and a second contact surface 151b, which is horizontally and vertically displaced with respect to the first surface 151a, to permit the piston rod 123b an additional increment of travel in the horizontal direction. The stop member 153 comprises a single contact surface 153a for providing a still further increment of horizontal travel to the second piston rod 123b, and it, too, is vertically displaced with respect to the first two contact surfaces, 151a and 151b. Vertical positioning of the contact surfaces 151a, 151b, and 153a to be alignment with the piston rod 123b is effected by controlling the travel of the vertical pneumatic cylinder piston rod 145a by means of a pair of compressed air hoses 155 and 157.

Operationally, the piston rod of the horizontal probe positioning cylinder 95 is initially retracted so that the sample probe 33 is positioned immediately above the diluent reservoir 119 located adjacent the front wall of the housing 81. The vertical probe positioning cylinder 105 is selectively actuated so that its piston rod moves downwardly to place the end of the sample probe 33 in the diluent. At this time, the calibration cylinder 145 is actuated to position the first contact surface 151a in alignment with the second piston rod 123b of the pneumatic cylinder 123. As the piston rod 123b moves to contact the first contact surface 151a, the pump piston rod 129a is withdrawn from the reagent pump 129 and a predetermined volume of the diluent is aspirated into the sample probe 33.

Next, the vertical probe positioning cylinder 105 is operated to withdraw the sample probe 33 from the diluent reservoir 119, and the calibration cylinder 145 is actuated to move the second contact surface 151b into alignment with the piston rod 123b. As a result, when the pneumatic cylinder 123 is actuated so that its second piston rod 123b moves to contact the second contact surface 151b, the sample probe 33, responsive to the reagent pump 129, aspirates a volume of air into the sample probe 33.

Subsequently, the horizontal probe positioning cylinder 95 is actuated to position the sample probe 33 directly over the sample cup 15, and the vertical probe positioning cylinder 105 is, in turn, actuated to insert the sample probe 33 into the specimen in the sample cup 15. The calibration cylinder 145 is then controlled to move its piston rod 145a upward so that the contact surface 153a of the second stop member 153 is aligned with the second piston rod 123b. The pneumatic cylinder 123 is subsequently actuated, and in response, the second piston rod 123b moves laterally until it reaches the contact surface 153a aligned therewith. As a result, the reagent pump 129 aspirates an aliquot test sample portion of the specimen from the sample cup 15 into the probe 33. Accordingly, as may be seen more clearly in FIG. 3A, an air space 159 separates the diluent 161 from the test sample 163 to prevent mixing of the diluent and the specimen in the sample probe 33. Moreover, the horizontal displacement between the first contact surface 151a and the second contact surface 151b of the first calibration stop member 151 determines the amount of space or air gap between the diluent 161 and the test sample 163, while the horizontal displacement of the contact surfaces 151a and 153a, respectively, determine the amount of diluent and specimen drawn into the pickup probe 33.

The vertical probe positioning 105 is then actuated to withdraw the probe 33 from the sample cup 15 and the horizontal probe positioning cylinder 95 is further actuated to move the sample probe 33 outwardly from the housing 81 until it is in position in vertical alignment with the reaction vessel 39. Responsive to the vertical probe positioning cylinder 105, the probe 33 is then lowered into the reaction vessel 39 located in the block 41 at the aspirating position 41a. Subsequently, the pneumatic cylinder 123 is actuated so that the second piston rod 123b is withdrawn from contact with the stop members 151 and 153, and the reagent pump 129 responds accordingly by pumping the contents of the probe 33 into the reaction vessel 39, the diluent washing all traces of the specimen from the sample probe 33.

Finally, the sample probe 33 is withdrawn from the reaction vessel 39 and the horizontal probe positioning cylinder 95 withdraws the probe 33 into the housing 81 to its initial position in vertical alignment with the diluent reservoir 119.

As previously described, after the aliquot portions of the specimen and the diluent comprising the test samples have been loaded into the reaction vessels 39, the samples are transported from the aspirating station 31 to the determinating station 45 for analysis. While the reaction vessels 39 are en route to the determinating station 45, the reagents necessary to perform the particular tests or analyses being run on the several test samples drawn from a particular specimen are selectively added to the test samples by a programmable reagent pumping station 47 at various predetermined points along the way. Referring now to FIGS. 4 and 5, the programmable reagent pumping station 47 is hereinafter described in greater detail. To simplify the description of the reagent pumping station 47 and its operation, only two intermediate block positions 41d and 41e and the blocks positioned thereat are illustrated in FIG. 4. It will be apparent by reference to FIGS. 1 and 2 that additional blocks 41 will be positioned between and on opposite sides of the two reagent blocks 41d and 41e shown in FIG. 4.

In the present embodiment, the pumping apparatus comprises forty-eight reagent pumps 49, each of which is operated by a corresponding pneumatic cylinder 167 (FIG. 5). Each reagent pump 49 is supplied with a particular chemical reagent by a flexible hose line 169 from one of the several reagent supply vessels 171. Each supply vessel 171 contains one of the reagents required for the various tests being run.

The timing for adding the reagents, as previously described, is controlled by a plurality of microswitches 53, each having a switch actuating element 53a for closing the microswitch 53 when contact is made with the sample cups 15 being returned in the return track 13b. Since the sample cup 15 from which the aliquot test samples are obtained is returned along the return track 13b at the same rate and in parallel with the corresponding block 41 carrying the aliquot test sample portions, the microswitches 53 are used to control the reagent pumps 49 to effect the addition of one or more selected reagents when the block 41 pauses at the position corresponding to a particular microswitch 53.

Each microswitch 53, in turn, controls a solenoid-compressed air valve 173 coupled to the microswitch 53 by an electrically conductive control line 175. An air hose 177 couples a compressed air source 179 to the valve 173, and accordingly, the valve 173 couples a stream of compressed air through an air hose 181 to a distribution manifold 183 whenever the microswitch 53 is actuated. The distribution manifold 183 has a single input 183a connected to the solenoid valve 173 and five outputs, 183b–183f, inclusive. Any or all of the distribution manifold outputs 183b–183f may be coupled to the corresponding input 185a of a pump manifold 185 by respective air hoses 187 as shown in FIG. 4. Each pump manifold 185, in turn, has three outputs 185b, 185c and 185d available to supply compressed air to the pneumatic cylinder 167 associated with the corresponding reagent pump 49. The reagent lines 51, positioned with their open ends immediately above and aligned with the selected ones of the reaction vessels 39 in the corresponding block 41 to which the reagents are to be added at that particular intermediate position, couple the reagents pumped from each of the enabled pumps 49 to the reaction vessels 39.

In running certain combinations of tests all three pumps 49 coupled to the outputs of the pump manifold 185 associated with a particular intermediate block position may already be used when, in fact, other reagents must be added to other reaction vessels at that precise point. Thus, the distribution manifold 183 provides additional capability for adding reagents at any intermediate block position as required. For illustrative purposes, in the embodiment shown in FIG. 4, each of the three pumps 49 connected to the pump manifold outputs 185b–185d, respectively, is in use. It will be apparent, however, in view of the description of the present invention, that if additional pumps 49 are required to add reagents to reaction vessels 39 at that position, one or more of the unused distribution manifold outputs, i.e., 183c–f, inclusive, is cross-coupled to the input of any of the other pump manifolds not in use. Thus, if at any particular block position more than three reaction vessels 39 require that a reagent be added, additional pumps 49 may be utilized by coupling an air hose from one of the remaining distribution manifold outputs, e.g., output 183f, to the input of a second pump manifold 193, as illustrated by the dashed line 191 in FIG. 4, and coupling the corresponding reagent lines 51 to the appropriate reaction vessels 39 in the manner shown by the dashed line 51. Thus, whereas each particular station has only three pumps 49 associated therewith, by proper interconnection, or programming, other pumps 49 can be utilized to introduce reagents to more than three reaction vessels 39 in a block 41 at any particular block position.

An illustrative reagent pump 49 and its associated pneumatic actuating cylinder 167 are shown in greater detail in FIG. 5. There it may be seen that the pneumatic cylinder 167 and the reagent pump 49 are mounted on a horizontal support member 195. The piston rods, 167a and 49a, of the pneumatic cylinder 167 and the reagent pump 49, respectively, are interconnected by a rocker arm 197 pivoted about point 199 so that movement of the cylinder piston rod 167a is translated to the reagent pump piston rod 49 to position the reagent pump piston 49b. The movement of a second pneumatic cylinder piston rod 167b extending from the top end of the cylinder is limited by an adjustment screw 201 supported in a frame 203 mounted on the support member 195. The adjustment screw 201 is adjusted to permit a predetermined amount of travel by the piston rod 167b. This, in turn, determines the travel of the reagent pump piston 49b, and thus the amount of reagent added.

Accordingly, when the pneumatic cylinder 167 is actuated the piston rod 167b moves to contact the adjustment screw 201. The other piston rod 167a extending from the lower end of the pneumatic cylinder 167, in turn, pulls the reagent pump piston 49b downward, drawing a predetermined amount of reagent into the pump 49, through a check valve 205 coupling the reagent supply vessel 171 to the reagent pump 49 immediately adjacent the top end of the pump 49. After the reagent is loaded in the pump 49, the air source 179 (FIG. 4) is controlled by the microswitch 53 contacting the sample cup 15 to force the pneumatic cylinder piston rods 167a and 167b downward and thereby move the reagent pump piston 49b upward to force the reagent out of the pump 49 into the reagent line 51 which delivers the reagent to the reaction vessel 39 to react with the test sample.

Upon reaching the determinating station 45 after all of the reactions have been completed, the reacted samples are tested and analyzed. As illustrated generally in FIGS. 1 and 2 the determinating apparatus comprises a plurality of pickup probes 55 such as the one shown more particularly in FIG. 6. There the probe 55 is shown positioned on a platform 207 which is movable in the up-down direction by a vertically positioned pneumatic cylinder 209 mounted on a stationary frame member 211 of the determinating station. The piston rod 209a of the cylinder is coupled to the movable platform 207 to effect movement of the platform and thereby selectively lower the probes 55 into the reaction vessels 39 to aspirate an aliquot portion of the reacted sample from the vessel 39. A flexible tube 213 couples the reacted test sample to a corresponding 15 mm. flow-through cuvette 215. A massaging pump 217 in the output line 219 from the cuvette 215 aspirates the reacted sample from the reaction vessel 39 and pumps the sample through the line 213 and the cuvette 215.

With reference to FIGS. 6 and 7, a plurality of the U-shaped flow-through cuvettes 215 are mounted in corresponding housings 210 supported by yoke members 221 on a plate member 222. The cuvettes 215 are arranged in a circle about a double filament lamp 223 located at the center of the circle. The lamp 223 emits light radially therefrom toward the cuvettes 215, and the horizontal bottom portion of each U-shaped cuvette 215 is aligned radially with the lamp 223 so that the light is transmitted therethrough. A light filter 225 mounted in a support member 227 is interposed between the lamp 223 and the cuvette 215 to filter out undesirable light frequencies. A spectrophotometer photocell 229 is positioned on the other side of the cuvette 215 in a housing 231 which, in turn, is inserted into a mounting member 233. The photocell 229 is aligned with the lamp 223, the filter 225, and the cuvette 215 to monitor the characteristics of the light passing through the reacted test sample in the cuvette 215. The test information detected by the photocell 229 is then coupled to a printer where it is printed out on a paper tape, or alternatively, the information is coupled to a computer for tabulation and comparison. Thus, a single lamp 223 provides the light output required by the several photodetector test units. Since the lamp 223 is of the double filament variety, one filament serves as a backup which can be enabled if the other filament burns out. A light detector 235 mounted in proximity to the lamp 223 monitors the light output from the lamp 223 and enables the second filament if the first filament fails, thereby removing the possibility of having to stop the analyses being performed to replace a burned out bulb.

At the same time the reacted test samples are scanned by the photocells 229, a portion of the original specimen reamining in the sample cup 15 on the return track 13b is aspirated and subjected to a flame test to assay the sodium and potassium components of the specimen. The results are obtained and printed out simultaneously with the other test results for the particular specimen under test. In particular, the flame photometer apparatus, shown generally in FIGS. 1 and 2 and more particularly in FIGS. 8–10, inclusive, comprises a pickup probe 57 positioned over the return track 13b for aspirating a portion of the original liquid specimen remaining in the sample cup 15. A coupling member 237 mounts the probe 57 on the end of the piston rod of a vertically positioned pneumatic cylinder 239 mounted on a support member 241 so that the probe 57 is movable in the up-down direction. When the sample cup 15 containing the specimen to be tested is positioned directly below the sample probe 57, the pneumatic cylinder 239 is actuated to move the probe 57 downward into the specimen. A pump 241 interposed in a flexible hose line 243 between the probe coupling member 237 and the flame photometer apparatus 59 aspirates a portion of the liquid specimen from the sample cup 15 and pumps it to the flame photometer 59. The support member 241 is movable in the horizontal direction so that the probe 57 can then be positioned over and lowered into a reservoir 245 containing a wash solution to clean the probe 57.

As may be seen more clearly in FIGS. 9 and 10, the flame photometer apparatus 59 comprises a cylindrical, perforated combustion chamber 247 mounted in a housing 249. The aspirated specimen sample is sprayed into the chamber 247 through a nozzle 251 coupled to the flexible hose line 243 while a flammable gas vapor is coupled to the combustion chamber 247 under pressure and released into the chamber through holes 243 in a manifold 255. A sparking device 257 such as a coil or spark plug is located immediately adjacent the nozzle 251 and the manifold 255 between the chamber 247 and the housing 249 to ignite the gaseous vapor and burn the specimen. A chimney 259 is provided at the top end of the housing 249 to release the combusted gases to the atmosphere.

Three photometers 261 are mounted on the photometer housing 249 to monitor the spectral characteristics of the burning specimen sample through corresponding apertures 249a in the housing 249 and assay, for example, the sodium and potassium components. The photometers 261 are, in turn, coupled to the printer, or alternatively to a computer, to print out the test results on the paper tape simultaneously with the test results from the determinating apparatus.

FIGS. 11 and 12 illustrate in more detail the X–Y pickup apparatus shown generally in FIG. 1. In particular, the apparatus comprises a pickup mechanism, identified generally at 67, mounted adjacent the end of a slide rail 265 which is slidably mounted in a sleeve member 267, permitting the pickup mechanism 67 to be positionable in the arbitrarily designated X direction by an X positioning apparatus. The sleeve member 267, in turn, is mounted on a platform 269 which rides on a pair of rails 271 extending in the Y direction and which can be slidably repositioned at one-inch increments in the Y direction by a Y positioning apparatus.

The Y positioning apparatus includes a pair of piggyback pneumatic cylinders 273 and 275 having respective piston rods 273a and 275a with four-inch strokes extending from opposite ends thereof. The end of piston rod 273a is affixed to a stationary point on the frame 277 while the other piston rod 275a is joined to the two-inch piston rod 279a of a third pneumatic cylinder 279. A one-inch cylinder 281 is coupled to the other end of the two-inch cylinder 279. The piston rod 281a of the one-inch cylinder is attached to the slidable sleeve member 267, and accordingly, it will be understood that by selectively extending the piston rods of the various pneumatic cylinders 273, 275, 279, and 281, incremental changes in the Y direction can be made at one-inch intervals from zero to eleven inches.

An identical arrangement comprising pneumatic cylinders 283, 285, 287 and 289 comprising the X positioning apparatus is also provided, except that the piston rod 283a of one four-inch pneumatic cylinder 283 is fixed to the remote end of the platform 269 while the one-inch piston rod 289a is coupled to the end of the slide rail 265 by a coupling member 291. Thus, the X positioning apparatus is effective to reposition the slide rail 265 at one-inch increments from zero to eleven inches in the X direction. Accordingly, the pickup apparatus can be sequentially repositioned from the sample cup pickup position, identified generally at 293, in the return track 13b to one of the one hundred points comprising a ten-inch by ten-inch grid on the sample cup tray 69.

The pickup mechanism 67, shown in detail in FIG. 12, includes a first vertically positioning pneumatic cylinder 295 mounted on a plate 297 affixed near the end of the slide rail 265. The piston rod 295a of the cylinder extends downwardly through an aperture in the plate 297. Attached to the end of the piston rod 295a is a stationary member 299 having a laterally disposed claw 301 at its bottom end and a pivoted member 303 also extending downwardly, but angularly, from a pivot point 305 on the upper portion of the stationary member 299. The pivoted member 303 has a laterally disposed claw 307 at its bottom end in opposing relation with the claw 301 of the stationary member 299. The pneumatic cylinder 295 is selectively enabled to lower the pickup mechanism 67 over the sample cup 15 at the pickup position 293 on the return track 13b. Lateral movement of the pivoted member 303 toward the stationary member 299 is effected by a spring 309 extending between the pivoted member 303 and the stationary member 299 to bring them in proximity to grasp the sample cup 15. A pneumatic cylinder 311 mounted horizontally on the stationary member 299 has a piston rod 311a extending through an aperture in the member 299 to contact the movable pivoted member 303 and selectively push the members 299 and 303 apart to release the cup 15.

A second pneumatic cylinder 315 is positioned beside the first pneumatic cylinder 295. The stroke of its piston rod 315a, however, is approximately an inch shorter than that of piston rod 295a. Also, the end of the rod 315a is not attached to the top of the stationary member 299, but rather rod 315a merely contacts the member 299 when the rod 315a is extended downwardly. This is necessary in the present embodiment because the top surface of the tray 69 is approximately one inch above the surface of the return track 13b. Accordingly, although the piston rod 295a of pneumatic cylinder 295 must be of sufficient length to permit the pickup mechanism 67 to grasp the cup 15 when it is in the return track 13b, the cylinder 295 would jam the pickup mechanism 67 into the tray 69 when the apparatus is positioned above the tray 69 to deposit a sample cup 15 therein. Thus, the second cylinder 315, having a shorter stroke, is provided to push the mechanism down a predetermined distance to deposit the sample cup 15 in the tray 69 without dropping the cup or jamming the cup into the tray.

Operationally, when a sample cup 15 reaches the pickup position 293 on the return track 13b, the pickup mechanism 67 is positioned over the cup 15 and the first pneumatic cylinder 295 is actuated so that its piston rod 295a is moved downward to lower the mechanism over the sample cup 15. Once the claws 301 and 307 of the stationary member 299 and the pivoted member 303, respectively, are positioned underneath or below the lip of the sample cup 15, the piston rod 311a is retracted so that the claw members 301 and 307 grasp the sample cup 15.

Simultaneously, a vertically disposed pneumatic cylinder (not shown) positioned immediately under the pickup position 293 extends its piston rod upwardly through a hole 318 in the bottom of the receptacle 11 to push the sample cup 15 from the receptacle 11 and into the pickup mechanism. A lid member 319 mounted between the pivoted member 303 and the stationary member 299 covers the cup 15 to prevent spillage. Once securely positioned in the pickup mechanism 67, the sample cup 15 is relocated in the X–Y direction by the X and Y positioning apparatus 67 and placed in a cavity 71 in the sample cup tray 69 in sequential fashion.

Figure 14:
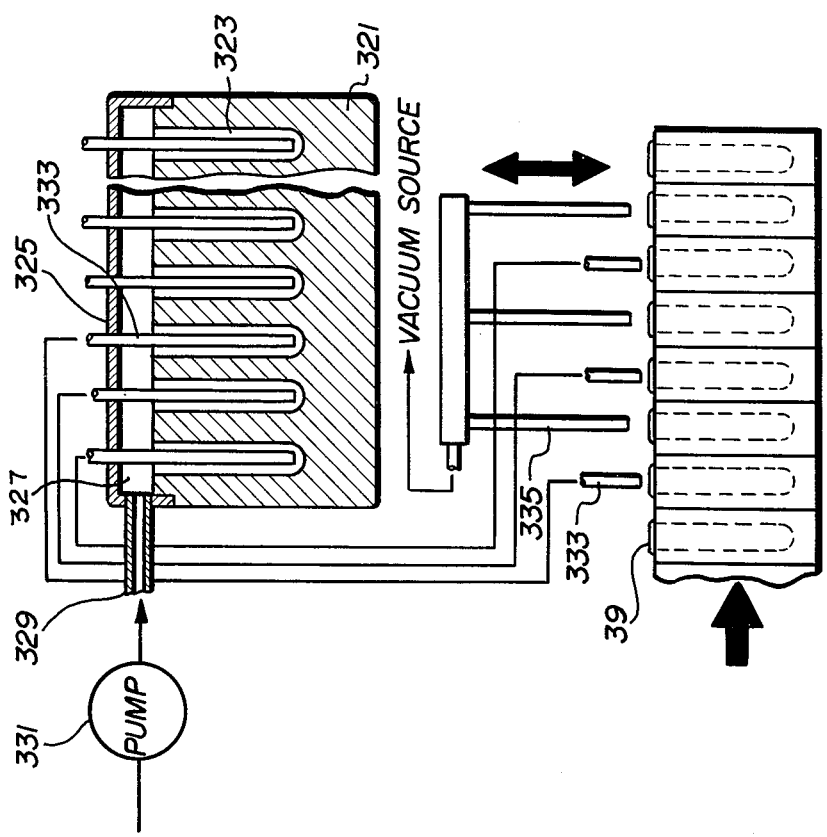
FIG. 14 is an elevational view in section and in schematic illustrating the washing apparatus in FIG. 13.
Figure 13:
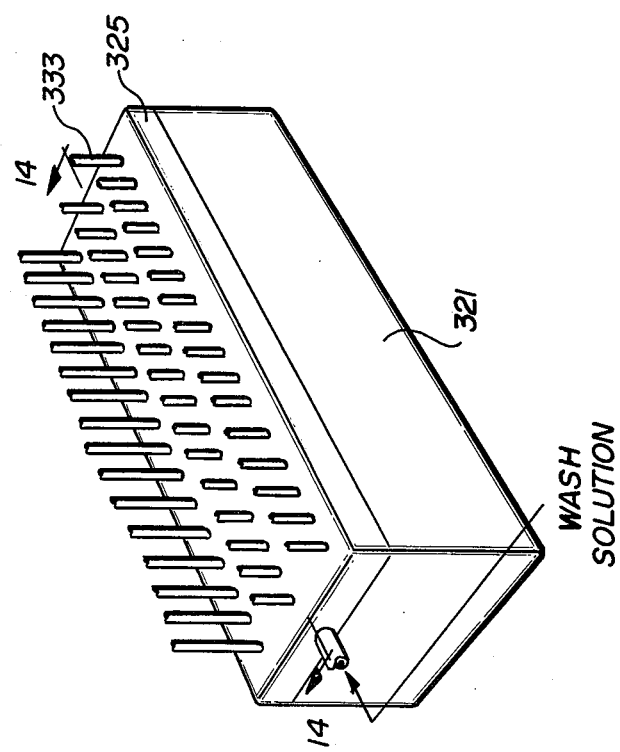
FIG. 13 is a perspective view illustrating the washing apparatus.

In FIG. 2 it may be seen that after the block 41 has reached the determinating station 45 and the reacted test samples have been aspirated from the reaction vessels 39, the block 41 is moved laterally to an adjacent position where the block 41 is then pushed in the opposite direction to return it to the aspirating station 31. During the return trip back to the aspirating station 31, the reaction vessels 39 are subjected to washing and drying operations conducted by the washing station 79. In particular, referring now to FIGS. 13 and 14, the washing station 79 comprises a block 321 having forty-eight cavities 323 therein arranged in three rows of sixteen cavities each. A cover 325 fits over the block 321 so that a small air space is provided in the space 327 above the block 321. An input 329 is coupled to a centrifugal pump 331 which pumps water and/or cleaning solution into the air space between the block 321 and the cover 325. The water is forced across the surface of the block 321, filling each cavity 323 with water. Individual lines or tubes 333 extend through the top cover 325 in sealed relationship therewith and extend down into the cavities 323. As water is pumped into the space 327 above the block 321, the water therein applies pressure to the water in the cavities 323 and forces the water up through the tubes 333 which, in turn, direct the water to three different washing positions, each comprising sixteen of the tubes 333, where the water is introduced into the reaction vessels 39.

Interspersed between the washing positions are three vacuum aspiration positions. That is, three rows of sixteen tubes 335 each are connected to a vacuum source to aspirate the water from the reaction vessels 39 in each block 41 after the alternate corresponding wash cycle is completed. Accordingly, the wash and aspirate cycle is repeated three times for each reaction vessel 39. At the end of the wash and aspirate cycles, the reaction vessels 39 are clean and ready to accept a new test sample. Thus, when the reagent block 41 reaches the end of its return travel, it is moved laterally into position adjacent the aspirating station 31 to accept a new aliquot test sample portion.

Accordingly, there has been shown and described an apparatus for automatically performing a plurality of determinations or analyses of liquid specimens in accordance with the principles of the present invention. The particular embodiment of the automated chemical analyzer apparatus just described is capable of making from 1 to 18 determinations on each specimen while analyzing up to 120 specimens per hour, performing colorimetric endpoint, 3-points ultraviolet kinetic, and flame photometric analyses. The apparatus is easily and quickly programmed by rerouting the delivery lines and the lines between the distribution manifolds and the pump manifolds in te reagent pumping station, making the analyzer apparatus a flexible tool which can be adapted for many uses. And as previously described, the automatic positive sample identification means provided reduces, if not eliminates, the errors commonly resulting from manual handling of the specimens.

While a particular embodiment of the present invention has been shown and described, it will be obvious to those skilled in the art that various changes and modifications may be made without departing from the invention in its broader aspects. Accordingly, the aim in the appended claims is to cover all such changes and modifications which may fall within the true spirit and scope of the invention.

I claim:
1. Apparatus for automatically performing multiple chemical analyses of a plurality of discrete liquid specimens comprising:

means comprising a plurality of sample containers, each of the sample containers initially containing one of the specimens;

means comprising a plurality of reaction vessels in each of several parallel aligned rows;

means for loading a plurality of specimen test samples from each of the sample containers into a corresponding one of the rows of reaction vessels, the loading means including means for automatically aspirating the plurality of test samples from each of the sample containers and means for sequentially conveying the sample containers to and from the aspirating means, the aspirating means discharging the plurality of test samples aspirated from the sample container into the corresponding row of reaction vessels before aspirating the test samples from the sample container subsequently conveyed to the aspiration means;

means for transporting the several rows of reaction vessels in a continuous sequence from the aspirating means to a determinating station, the conveying means conveying each of the sample containers from the aspiration means in parallel with the corresponding row of reaction vessels containing the test samples aspirated from the sample container;

means comprising a plurality of switching devices being sequentially enabled by each of the sample containers being conveyed from the aspiration means for selectively adding reagents to certain ones of the reaction vessels, each of the switching devices being effective to cause one or more of the reagents to be added to selected ones of the reaction vessels in the row corresponding to the sample container enabling the switching device; and means for automatically analyzing the reacted test samples at the determinating station and outputting the results of the analyses.

2. Apparatus in accordance with claim 1 wherein the aspiration means comprises a plurality of independently operable aspirating apparatus, each of the aspirating apparatus having an associated aspiration probe and being selectively actuable to aspirate one of the plurality of test samples from the sample container conveyed to the aspiration means and discharge the test sample into the corresponding reaction vessel, and wherein the conveying means includes means for transferring the sample container sequentially past the plurality of aspirating apparatus, the transfer means stopping at each aspirating apparatus while the test sample is aspirated from the sample container before proceeding to the next aspirating apparatus.

3. Apparatus in accordance with claim 1 including means for aspirating a portion of the specimen contained in the sample containers being conveyed from the aspiration means in parallel with the rows of reaction vessels being transported to the determinating station and flame photometer means for burning the aspirated specimen and monitoring the spectral characteristics data of the burning specimen, the flame photometer means coupling the spectral characteristics data to the analyzer means for outputting the data with the other results of the analyses of the reacted specimen test samples.

4. Apparatus in accordance with claim 1 including sample registration means for receiving the sample containers and means for removing the sample containers from the means conveying the sample containers from the aspiration means and placing the sample containers in the sample registration means in sequential order after the corresponding row of reaction vessels has reached the determinating station.

5. Apparatus in accordance with claim 1 wherein each of the aspirating apparatus includes means for positioning the associated aspiration probe, the positioning means inserting the probe into the specimen in the sample container to aspirate the sample therefrom and repositioning the probe to be over a corresponding one of the reaction vessels to discharge the test sample into the reaction vessel.

6. Apparatus in accordance with claim 5 wherein the aspirating apparatus include means for diluting the test samples and flushing the test sample from associated probes into the corresponding reaction vessels with a diluent, the diluent cleansing the probes in preparation for aspiration of the next test samples.

7. Apparatus in accordance with claim 1 wherein the reagent adding means comprises pump means having output means selectively positioned to add reagents to certain ones of the reaction vessels at predetermined times before the reaction vessels reach the determinating means as the rows of reaction vessels are transported from the aspiration means to the determinating station, the pump means being responsive to the switch devices to add reagents to certain ones of the reaction vessels in each row as the sample container corresponding to the row enables the switching device.

8. Apparatus in accordance with claim 7 wherein the reagent adding means comprises a plurality of the pump means, a plurality of multi-output distribution manifold means, each of the distribution manifold means being associated with a corresponding one of the switching devices and responsive thereto, and a plurality of pump manifold means, each of the pump manifold means having an input selectively coupled to one of the outputs of one of the distribution manifold means and a plurality of outputs selectively coupled to associated ones of the plurality of pump means, the output means of each of the pump means being positioned over certain ones of the reaction vessels in the row of reaction vessels corresponding to the switching device controlling the distribution manifold means coupled to the pump manifold means associated with the pump means, the distribution manifold means associated with any of the switching devices and any number of the pump manifold means being selectively intercoupled to provide a plurality of the pump means for adding reagents to the reaction vessels in the row of reaction vessels associated with the switching device.

9. Apparatus in accordance with claim 1 wherein the means for transporting the several rows of reaction vessels from the aspiration means to the determinating station and back to the aspiration means comprises a corresponding number of block means, each of the block means having cavities along the length thereof for holding one of the rows of reaction vessels, means for pushing the several block means in continuous sequence in direction normal to the lengths of the several block means from the aspiration means to the determination station, means for pushing the block means laterally at the determinating station after the reacted test samples have been analyzed, means for pushing the block means from the lateral position adjacent the determination station back to a position immediately adjacent and lateral to the position adjacent the aspiration means where the test samples are loaded into the reaction vessels, and means for pushing the block means laterally into the position adjacent the aspiration means.

10. Apparatus in accordance with claim 9 including a controlled temperature bed having selectively variable heating zones for supporting the block means and heating the test samples to required temperatures at various points between the aspiration means and the determinating station.

11. Apparatus in accordance with claim 1 wherein the reacted test sample analyzing means includes means for aspirating the reacted test samples from the reaction vessels at the determinating station and coupling the aspirated reacted test samples to the means for analyzing the reacted test samples.

12. Apparatus in accordance with claim 11 wherein the analyzing means comprises a lamp, a plurality of flow-through cuvettes coupled to the aspirating means, the reacted test samples flowing through corresponding ones of the cuvettes and each of the cuvettes being radially aligned with the lamp, and a plurality of spectrophotometer photocells for detecting the characteristics of the light passing through the reacted test samples in the cuvettes.

13. Apparatus in accordance with claim 12 wherein the lamp is a double filament lamp having first and second filaments and including light detector means for monitoring the light from the double filament lamp and enabling the second filament if the first filament stops emitting light.

14. Apparatus in accordance with claim 1 wherein the means for transporting the rows of reaction vessels from the aspiration means to the determinating station includes means for transporting the several rows of reaction vessels in a continuous sequence from the determinating station back to the aspiration means.

15. Apparatus in accordance with claim 14 including means for washing the reaction vessels with a washing liquid as the rows of reaction vessels are transported back to the aspiration means from the determinating station to receive other test samples.

16. Apparatus in accordance with claim 15 wherein the washing means comprises a plurality of tubes, a block having a corresponding plurality of cavities therein, means for covering the block so that a small air space exists between the cover means and the block with which the plurality of cavities communicate, each one of the plurality of tubes extending through the cover means into a corresponding one of the cavities, means for pumping a washing liquid into the air space between the block and the cover means to force the washing liquid into the cavities and out the tubes, and means for positioning the tubes over the plurality of reaction vessels to wash the reaction vessels as the rows of reaction vessels are transported back to the aspiration means from the determinating station.

17. Apparatus in accordance with claim 15 including means for aspirating the washing liquid from the reaction vessels.

18. Apparatus in accordance with claim 1 wherein the conveying means includes a track for sequentially delivering the sample containers to the transfer means one at a time for transfer past the aspiration apparatus and a track for returning the sample container from the transfer means after the plurality of test samples have been aspirated therefrom, the sample container being conveyed in the return track in parallel with the row of reaction vessels containing the test samples aspirated from the sample container.

19. Apparatus in accordance with claim 18 wherein the transfer means comprises trolley means for carrying the sample container and reversing motive means for moving the trolley means from the delivery track, to the aspiration means, past the plurality of aspirating apparatus, the motive means there reversing to move the trolley means back to the delivery track, the trolley means pausing at the return track while the sample container is moved from the trolley means into the return track.

20. Apparatus in accordance with claim 18 wherein the conveying means includes an end track interconnecting the other ends of the delivery track and the return track and means for moving the sample containers along the tracks to and from the transfer means in a continuous sequence.

21. Apparatus in accordance with claim 20 including receptacles for carrying the sample containers in the tracks and the transfer means, adjacent ones of the receptacles abutting each other in the tracks in a continuous sequence and wherein the means for moving the sample containers along the tracks comprises pneumatic means aligned with the ends of the return track, the end track and the delivery track, the pneumatic means aligned with the delivery track pushing the receptacles along the delivery track to load the receptacle at the other end of the track into the transfer means, the pneumatic means aligned with the end track pushing a receptacle at the other end of the end track into the delivery track at the position adjacent the delivery track pneumatic means, and the pneumatic means aligned with the return track subsequently pushing the receptacle previously loaded into the transfer means from the transfer means into the return track and causing the receptacle at the other end of the return track to be pushed into position in the end track adjacent the end track pneumatic means.

22. Apparatus in accordance with claim 21 including means comprising a tray having a plurality of cavities therein arranged in X–Y grid pattern in arbitrarily designated X and Y directions and including X–Y positioning means for initially positioning the pick-up means at a pick-up position over the means conveying the sample containers from the aspiration means to pick up one of the sample containers the corresponding receptacle and for repositioning the pick-up means over one of the cavities in the tray whereupon the pick-up means releases the sample container into the cavity, the X–Y positioning means directing the sample containers received sequentially from the conveying means to the cavities in the X–Y grid pattern in sequential order.

* * * * *